United States Patent [19]

Blaney et al.

[11] Patent Number: 4,533,498
[45] Date of Patent: Aug. 6, 1985

[54] COMPOUNDS

[75] Inventors: Francis E. Blaney, London; Michael S. Hadley, Sawbrideworth; Francis D. King, Newport; Eric A. Watts, Harlow, all of England

[73] Assignee: Beecham Group p.l.c., Brentford, England

[21] Appl. No.: 574,089

[22] Filed: Jan. 26, 1984

[30] Foreign Application Priority Data

Jan. 29, 1983 [GB] United Kingdom ............. 8302483

[51] Int. Cl.$^3$ ............................................. A61K 31/54
[52] U.S. Cl. .............................. 260/243.3; 260/239 B; 260/239 BF; 260/330.3; 260/330.9; 544/297; 544/300; 544/301; 544/310; 544/311; 544/316; 544/317; 544/319; 544/321; 544/324; 544/325; 544/327; 544/328; 544/329; 544/331; 544/332; 544/333; 544/334; 544/335; 548/452; 548/465; 548/467; 424/244; 424/251; 424/263; 424/274
[58] Field of Search ......... 260/239 B, 239 BF, 330.3, 260/330.9, 243.3; 544/297, 300, 301, 310, 311, 316, 317, 319, 321, 324, 325, 327, 328, 329, 331, 332, 333, 334, 335; 546/122; 548/452, 465, 467; 424/244, 251, 263, 274

[56] References Cited

U.S. PATENT DOCUMENTS 4,273,778  6/1981  Hadley et al. ................... 424/267
4,350,691  9/1982  Hadley et al. ................... 424/267
4,352,802 10/1982  Blaney ......................... 424/248.54

FOREIGN PATENT DOCUMENTS 13138  7/1980  European Pat. Off. .
31219  7/1981  European Pat. Off. .
41817 12/1981  European Pat. Off. .

OTHER PUBLICATIONS

Law et al, J. Hetero Chem., 15 (2), Mar., 1978, pp. 273-280.
Cava et al., "A New Isoquinuclidine Synthesis, A New Route to dl-Dioscorone", J. Org. Chem., 30, 3772 (1965).
Krow et al., "Dioscorone, Regioselective Oxymercuration of 2-Azabicyclo[2.2.2]oct-5-ene," Syn. Commun., 2 (4) 211 (1972).
Protais et al., "Climbing Behavior Induced by Apomorphine in Mice: A Psychopharmacology, 50, 1-6 (1976).

Primary Examiner—Maurice J. Welsh
Attorney, Agent, or Firm—James F. Haley, Jr.; Paul H. Ginsburg

[57] ABSTRACT

Compounds of formula (I), pharmaceutically acceptable salts, quaternary derivatives and N-oxides thereof, and pharmaceutically acceptable solvates of any of the foregoing:

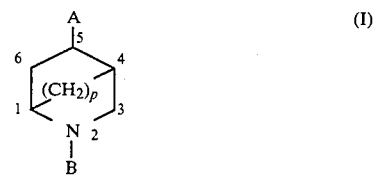

wherein
p is 1 to 3;
B is $C_{1-7}$ alkyl, $C_{3-8}$ cycloalkyl, $C_{3-8}$ cycloalkyl-$C_{1-2}$ alkyl, or a group $(CH_2)_tR_{11}$ where t is 1 or 2 and $R_{11}$ is thienyl or furyl optionally substituted or is phenyl optionally substituted; and
(i) A is a group of formula (II):

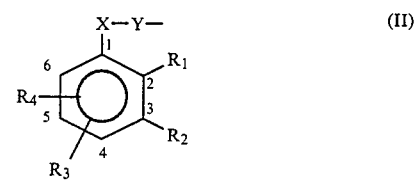

in which either
(a) one of X and Y is CO and the other is NH; or X is CO and Y is $NR_6$; and or
(b) one of X and Y is CO and the other is NH; or
(ii) A is a group of formula (III):

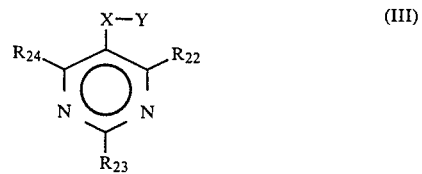

in which one of X and Y is CO and the other is NH, having useful pharmacological properties, pharmaceutical compositions containing them, a process and intermediates for their preparation, and the use of the compounds.

11 Claims, No Drawings

COMPOUNDS

This invention relates to novel compounds having useful pharmacological properties, to pharmaceutical compositions containing them, to a process and intermediates for their preparation, and to the use of the compounds.

U.S. Pat. No. 4,273,778, European Pat. No. 13138 and European Patent Publications 31219 and 41817 disclose compounds having an azabicyclic side chain and possessing dopamine antagonist activity.

A class of compounds having a novel azabicyclic side chain has been discovered. These compounds have dopamine antagonist activity.

Accordingly, the present invention provides a compound of formula (I), or a pharmaceutically acceptable salt, quaternary derivative or N-oxide thereof, or a pharmaceutically acceptable solvate of any of the foregoing:

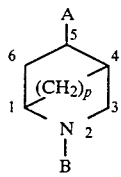

(I)

wherein
p is 1 to 3;
B is $C_{1-7}$ alkyl, $C_{3-8}$ cycloalkyl, $C_{3-8}$ cycloalkyl-$C_{1-2}$ alkyl, or a group $(CH_2)_t R_{11}$ where t is 1 or 2 and $R_{11}$ is thienyl or furyl optionally substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolysable acyloxy; and
(i) A is a group of formula (II):

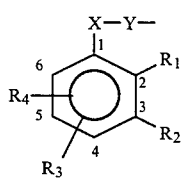

(II)

in which either
(a) one of X and Y is CO and the other is NH; and $R_1$ is selected from halogen, $C_{1-6}$ alkyl, $C_{1-6}$ alkoxy, $C_{1-6}$ alkylthio, and amino optionally substituted by one or two groups selected from $C_{1-6}$ alkyl, $C_{3-8}$ cycloalkyl, $C_{3-8}$ cycloalkyl $C_{1-4}$ alkyl, phenyl and phenyl $C_{1-4}$ alkyl groups or optionally N,N-disubstituted by $C_{4-5}$ polymethylene; or X is CO and Y is $NR_6$ where $R_1$ and $R_6$ together are $C_{1-2}$ alkylene; and either $R_2$, $R_3$ and $R_4$ are each independently selected from the class of hydrogen, halogen, $CF_3$, $C_{1-6}$ alkyl, $C_{1-6}$ alkoxy, $C_{1-6}$ alkylthio, $C_{1-7}$ acyl, $C_{1-7}$ carboxylic acylamino, $C_{1-6}$ alkylsulphonylamino, N-($C_{1-6}$ alkyl-sulphonyl)-N-$C_{1-4}$ alkylamino, $C_{1-6}$ alkylsulphonyl, $C_{1-6}$ alkylsulphinyl, hydroxy, nitro, or amino, aminocarbonyl, aminosulphonyl, aminosulphonylamino or N-(aminosulphonyl)-N-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl and phenyl $C_{1-4}$ alkyl or optionally N,N-disubstituted by $C_{4-5}$ polymethylene; or one of $R_2$, $R_3$ and $R_4$ is selected from the foregoing class and the remaining two of $R_2$, $R_3$ and $R_4$ when on adjacent atoms are together $C_{1-2}$ alkylenedioxy; or (b) one of X and Y is CO and the other is NH; $R_1$ and $R_2$ together are $C_{1-2}$ alkylenedioxy or $C_{1-2}$ oxyalkylenethio, or $C_{2-3}$ alkyleneoxy in which the oxygen atom is attached to the ring at the 2-position; as depicted in formula (II); and $R_3$ and $R_4$ are each independently selected from the class of values recited hereinbefore for $R_2$, $R_3$ and $R_4$ in paragraph (i) (a) hereinbefore or when on adjacent atoms are together $C_{1-2}$ alkylenedioxy; or (ii) A is a group of formula (III):

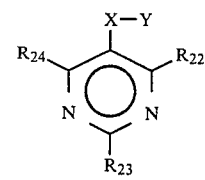

(III)

in which
one of X and Y is CO and the other is NH; and
$R_{22}$, $R_{23}$ and $R_{24}$ are each independently selected from the class of values of the variables $R_2$, $R_3$ and $R_4$ are defined hereinbefore in paragraph (i) (a) in relation to formula (II), except $C_{1-2}$ alkylenedioxy.

In formula (I), p can be 1 or 2 and is often 2.

Examples of B when $C_{1-7}$ alkyl include as groups of interest $C_{1-3}$ alkyl such as methyl, ethyl and n- and iso-propyl. Within $C_{1-7}$ alkyl, $C_{4-7}$ alkyl are also of interest, especially those of the formula $(CH_2)_u R_9$ wherein u is 1 or 2 and $R_9$ is a secondary or tertiary $C_{3-6}$ alkyl group. Examples of $C_{4-7}$ alkyl include n-, sec- and tert-butyl, n-pentyl, n-heptyl, and iso-butyl, 3-methylbutyl, and tert-butylmethyl.

Examples of B, when $C_{3-8}$ cycloalkyl $C_{1-2}$ alkyl include in particular those wherein the cycloalkyl moiety is cyclohexyl or cyclopropyl.

Examples of B include cyclopropylmethyl, cyclobutylmethyl, cyclopentylmethyl, cyclohexylmethyl, cyclopropylethyl, cyclobutylethyl, cyclopentylethyl, cyclohexylethyl, tert-butylmethyl, iso-propylmethyl, iso-propylethyl and tert-butylethyl.

B may in particular be cyclopropylmethyl, cyclohexylmethyl, iso-propylmethyl, tert-butylmethyl or iso-propylethyl, preferably tert-butylmethyl.

Preferred examples of B, when —$(CH_2)_t R_{11}$, are those wherein t is 1. $R_{11}$ may be 2- or 3-thienyl or 2- or 3-furyl optionally substituted by one of $C_{1-4}$ alkyl, $C_{1-4}$ alkoxy, trifluoromethyl or halogen, or preferably is phenyl optionally substituted by one of $C_{1-4}$ alkoxy, trifluoromethyl, halogen, carboxy, esterified carboxy and $C_{1-4}$ alkyl optionally substituted by hydroxy, $C_{1-4}$ alkoxy, carboxy, esterified carboxy and in vivo hydrolysable acyloxy.

The following five paragraphs relate to substituents of $R_{11}$ groups as appropriate.

Examples of $C_{1-4}$ alkoxy substituents include methoxy, ethoxy and n- and iso-propoxy, in particular methoxy.

Examples of halogen substituents include fluoro, chloro and bromo, often in the 3- or 4- position, in particular chloro.

In optionally substituted $C_{1-4}$ alkyl substituents, examples of $C_{1-4}$ alkyl include methyl, ethyl, n- and iso-propyl, and n- and iso-, sec- and tert-butyl; methyl however is preferred. Examples of substituents of such alkyl groups include hydroxy, methoxy, ethoxy, n- and iso-propoxy, carboxy, esterified carboxy and in vivo hydrolysable acyloxy. The substitution preferably occurs on the terminal carbon atom of the alkyl group.

Examples of esterified carboxy groups include $C_{1-4}$ alkoxycarbonyl, such as methoxy-, ethoxy-, n- and iso-propoxycarbonyl, or phenoxycarbonyl or benzyloxycarbonyl optionally substituted in the phenyl ring by one or two substituents selected from $C_{1-4}$ alkyl, $C_{1-4}$ alkoxy, trifluoromethyl, halogen or nitro.

Examples of in vivo hydrolysable acyloxy groups include $C_{1-6}$ alkanoyloxy, for example acetoxy, propionoxy, n- and iso-butyroxy, and 2,3 dimethylpropanoyloxy, benzoyloxy or benzenesulphonyloxy either being optionally substituted in the phenyl ring by one or two substituents selected from $C_{1-4}$ alkyl, $C_{1-4}$ alkoxy, trifluoromethyl, halogen or nitro, or sulphonyloxy groups, for example $C_{1-6}$ alkanesulphonyloxy group, such as methanesulphonyloxy.

The most preferred examples of B, when $-(CH_2)_tR_{11}$, are those wherein t is 1 and $R_{11}$ is unsubstituted phenyl or monosubstituted phenyl. Examples of substituents include methyl, trifluoromethyl, fluoro, chloro and bromo, especially fluoro. Unsubstituted benzyl is an especially preferred example of B.

When A is a group of formula (II) and one of X and Y is CO and the other is NH, values for $R_1$ include $C_{1-6}$ alkoxy and $C_{1-6}$ alkylthio, in particular methoxy. In this embodiment of formula (II) one the $R_2$, $R_3$ and $R_4$ may be hydrogen and the other two may together be methylenedioxy or ethylenedioxy or may each independently be hydrogen, chloro, bromo, $CF_3$, methyl, methoxy, ethoxy, n- or iso-propoxy, methylthio, ethylthio, n- or iso-propylthio, formylamino, $C_{1-4}$ alkanoylamino such as acetylamino, propionylamino, n- or iso-butyrylamino, nitro, or amino or aminosulphonyl optionally N-substituted by one or two methyl groups.

Preferably the other two of $R_2$, $R_3$ and $R_4$ are independently hydrogen, chloro, bromo, methoxy, amino or aminosulphonyl optionally substituted as hereinbefore defined, $C_{1-6}$ alkylsulphonyl, $C_{1-6}$ alkylsulphinyl, $CF_3$ or methyl.

$R_2$ is preferably hydrogen, $R_3$ is preferably in the 4-position as defined in formula (II) and $R_4$ is preferably in the 5-position as defined in formula (II).

Particularly preferred values of $R_3$ include hydrogen, methoxy, amino, carboxylic $C_{1-7}$ acylamino and methyl, especially in the 4-position as defined. Particularly preferred values of $R_4$ include hydrogen, chloro, bromo, methoxy, aminosulphonyl optionally substituted as defined, $C_{1-6}$ alkylsulphonyl, $C_{1-6}$ alkylsulphinyl or $CF_3$, especially in the 5-position as defined.

When A is of formula (II) and X is CO and Y is $NR_6$ where $R_1$ and $R_6$ together are $C_{1-2}$ alkylene, preferred values of $R_1+R_6$ include $CH_2$.

In this case, it is generally preferred that $R_2$ is hydrogen, $R_3$ is in the 4-position as defined in formula (II) and $R_4$ is in the 5-position as defined in formula (II).

Particularly preferred values of $R_3$ include hydrogen, chloro and bromo, especially in the 4-position as defined. Particularly preferred values of $R_4$ include optionally substituted aminosulphonyl as defined, such as amino-sulphonyl, $C_{1-6}$ alkylsulphonyl, such as methylsulphonyl, $C_{1-6}$ alkylsulphinyl, such as methylsulphinyl, chloro and bromo, especially in the 5-position as defined.

When A is of formula (II), one of X and Y is CO and the other is NH and $R_1$ and $R_2$ are together a variety of divalent radicals as hereinbefore recited (including $C_{1-2}$ alkylenedioxy), $R_3$ is preferably in the 4-position as defined in formula (II) and $R_4$ is preferably in the 5-position as defined in formula (II).

Particularly preferred values of $R_3$ include hydrogen, methoxy, amino and methyl, especially in the 4-position as defined. Particularly preferred values of $R_4$ include hydrogen, chloro, bromo, methoxy, aminosulphonyl optionally substituted as defined, $C_{1-6}$ alkylsulphonyl, $C_{1-6}$ alkylsulphinyl or $CF_3$, especially in the 5-position as defined.

When A is of formula (III), values for $R_{22}$ and particularly preferred $R_{23}$ are as so described for $R_1$ and $R_3$ when A is of formula (II), and one of X and Y is CO and the other is NH.

$R_{24}$ is preferably hydrogen.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of quaternary derivatives of the compounds of formula (I) include the compounds quaternised by compounds such as $R_8$-Q wherein $R_8$ is $C_{1-6}$ alkyl, phenyl-$C_{1-6}$ alkyl or $C_{5-7}$ cycloalkyl, and Q is a radical corresponding to an anion of an acid. Suitable examples of $R_8$ include methyl, ethyl and n- and iso-propyl; and benzyl and phenethyl. Suitable examples of Q include halide such as chloride, bromide and iodide.

The compounds of formula (I) may also form pharmaceutically acceptable N-oxides.

The compounds of the formula (I), their pharmaceutically acceptable salts, quaternary derivatives and N-oxides may also form pharmaceutically acceptable solvates.

It will of course be realised that the compounds of the formula (I) are asymmetric and have at least three chiral centres, viz. those numbered 1, 4 and 5 in formula (I). The compounds may also have other chiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

From the aforesaid it will be seen that suitably the moiety A in formula (I) may be of any one formulae:

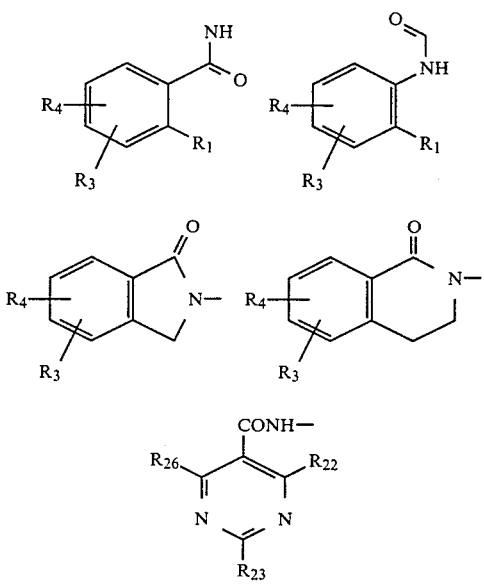

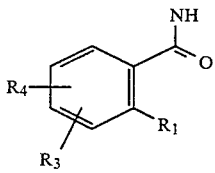

in particular one of formula:

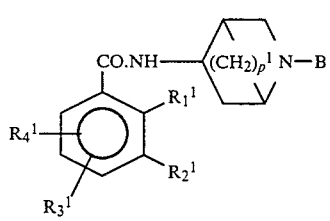

A group of compounds within formula (I) is of formula (IV):

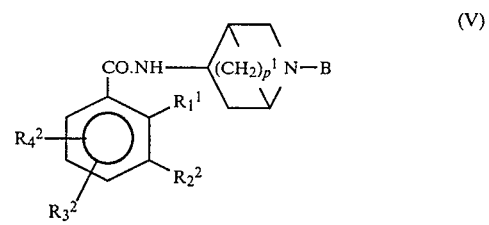

wherein either $R^1_1$ is $C_{1-6}$ alkoxy or amino optionally N-substituted by one or two groups selected from $C_{1-6}$ alkyl or $C_{3-8}$ cycloalkyl or optionally N,N-disubstituted by $C_{4-5}$ polymethylene; and one of $R^1_2$, $R^1_3$ and $R^1_4$ is hydrogen and the other two are independently selected from the class of hydrogen, amino optionally substituted by one or two $C_{1-6}$ alkyl groups or N,N-disubstituted by $C_{4-5}$ polymethylene, carboxylic $C_{1-7}$ acylamino, chloro, bromo, trifluoromethyl, hydroxy, $C_{1-6}$ alkoxy, $C_{1-6}$ alkylthio, $C_{1-6}$ alkyl, $C_{1-6}$ alkylsulphonyl, $C_{1-6}$ alkylsulphinyl or aminosulphonyl optionally N-substituted by one or two $C_{1-6}$ alkyl group or N,N-disubstituted by $C_{4-5}$ polymethylene; or $R^1_1$ and $R^1_2$ together are methylenedioxy or ethylenedioxy and $R_{13}$ and $R^1_4$ are the same or different and are selected from the class of substituent hereinbefore defined for $R^1_2$, $R^1_3$ and $R^1_4$; $p^1$ is 1 or 2; and B is as hereinbefore defined.

Examples of the variables and preferred variables are as so described for corresponding variables in relation to formulae (I) and (II).

A sub-group of compounds within formula (IV) is of formula (V):

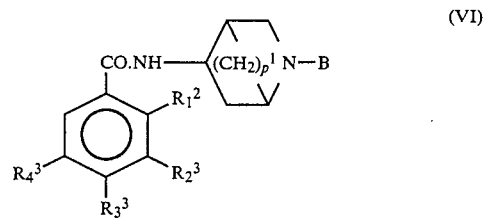

wherein $R^1_1$, $p^1$ and B are as defined in formula (IV); and one of $R^2_2$, $R^2_3$ and $R^2_4$ is hydrogen, and the other two are independently selected from hydrogen, amino, carboxylic $C_{1-7}$ acylamino, chloro, bromo, trifluoromethyl, hydroxy, $C_{1-6}$ alkoxy, $C_{1-6}$ alkylthio and $C_{1-6}$ alkyl.

Examples of the variables and preferred variables are as so described for corresponding variables in relation to formulae (I) and (II).

Particularly preferred compounds are those wherein $R^1_1$ is 2-methoxy, $R^2_2$ is hydrogen, $R^2_3$ is 4-amino, and $R^2_4$ is 5-chloro or 5-bromo, especially 5-chloro.

A second sub-group of compounds within formula (IV) is of formula (VI):

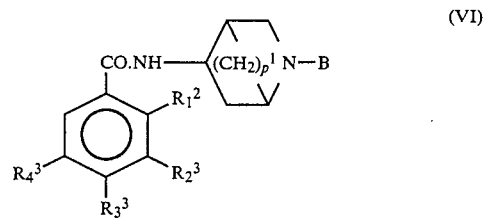

wherein $p^1$ and B are as defined in formula (V);

$R^3_3$ is hydrogen or amino.

$R^3_4$ is $C^{1-6}$ alkylsulphonyl, $C_{1-6}$ alkylsulphinyl, or aminosulphonyl optionally N-substituted by one or two $C_{1-6}$ alkyl groups or $C_{4-5}$ polymethylene; and either $R^2_1$ is $R^1_1$ as hereinbefore defined and $R^2_2$ is hydrogen; or $R^2_1$ and $R^3_2$ together are $C_{2-3}$ alkylenedioxy.

Suitable and preferred variables are as so described for corresponding variables in relation to formulae (I) and (II).

The invention also provides a process for the preparation of a compound of formula (I) wherein A is of formula (II), wherein the variables are as hereinbefore defined, which process comprises reacting a compound of formula (VII):

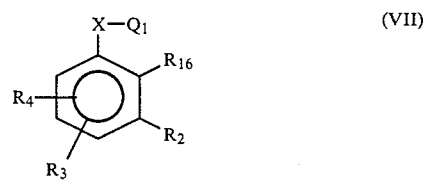

wherein
(i) X is CO and $Q_1$ is a group displaceable by a nucleophile, or X is NH and $Q_1$ is H;
$R_{16}$ is $R_1$ as defined in formula (II) when one of X and Y in formula (II) is CO and the other is NH; and
$R_2$, $R_3$ and $R_4$ are as defined in formula (II) when one of X and Y in formula (II) is CO and the other is NH; or
(ii) X is CO and $Q_1$ is a group displaceable by a nucleophile; and
$R_{16}$ is a group $(CH_2)_2CR_{17}R_{18}Q_2$ where v is 0 or 1, $R_{17}$ and $R_{18}$ are each H or together are O and $Q_2$ is a group displaceable by a nucleophile, or together with $Q_1$ is O; and
$R_2$, $R_3$ and $R_4$ are as defined in formula (II) when X is CO and Y is $NR_6$ as hereinbefore defined with a compound of formula (VIII):

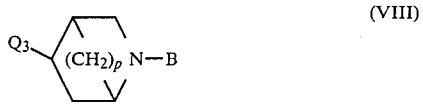

wherein B and p are as defined in formula (I); and
(i) when $Q_1$ in the compound of formula (VII) is a group displaceable by a nucleophile ortogether with $Q_2$ is O, $Q_3$ is $NH_2$;
(ii) when $Q_1$ in the compound of formula (VII) is H, $Q_3$ is $COQ_4$ where $Q_4$ is a group displaceable by a nucleophile;
when the desired compound of formula (I) is one wherein $R_1$ and $R_6$ together are $C_{1-2}$ alkylene, and $R_{17}$ and $R_{18}$ in the compound of formula (VII) are together O, reducing the compound resulting from the reaction of the compounds of formulae (VII) and (VIII); in a compound of formula (I) resulting from any process variant, optionally converting any $R_1$, $R_2$, $R_3$, $R_4$ or B group to another $R_1$, $R_2$, $R_3$, $R_4$ or B group respectively, and optionally forming a pharmaceutically acceptable salt, quaternary derivative or N-oxide of the resultant compound of formula (I). Examples of groups displaceable by a nucleophile include:
for $Q_1$, $Q_2$, and $Q_4$: halogen such as chloro and bromo; for $Q_1$, $Q_2$ when $R_{17}$ and $R_{18}$ together are oxo, and for $Q_4$: hydroxy, carboxylic acyloxy such as $C_{1-4}$ alkanoyloxy, $C_{1-4}$ alkoxycarbonyloxy and activated hydrocarbyloxy such as pentachlorophenoxy; and for $Q_2$ when $R_{17}$ and $R_{18}$ are each hydrogen: labile acyloxy such as tosyloxy, mesyloxy or triflate.
If a group $Q_1$, $Q_2$, or $Q_4$ is a halide, then the reaction is preferably carried out at non-extreme temperatures in an inert, non-hydroxylic solvent, such as benzene, dichloromethane, toluene, diethyl ester, THF or DMF. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.
If a group $Q_1$, $Q_2$ or $Q_4$ is hydroxy, then the reaction is preferably carried out in an inert non-hydroxylic solvent, such as dichloromethane, THF or DMF in the presence of a dehydrating catalyst, such as a carbodiimide, for example dicyclhexylcarbodiimide. For $Q_4$, the compound of formula (IX) is preferably in the form of an acid addition salt, such as the hydrohalide, for example the hydrochloride. The reaction may be carried out at any non-extreme temperature, such as $-10°$ to 100° C., for example, 0° to 80° C. Generally, higher reaction temperatures are employed with less active compounds whereas lower temperatures are employed with the more active compounds.

If a group $Q_1$, $Q_2$ or $Q_4$ is carboxylic acyloxy, then the reaction is preferably carried out in substantially the same manner as the reaction when $Q_1$, $Q_2$ or $Q_4$ is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature in the presence of an acid acceptor, such as triethylamine.

If a group $Q_1$, $Q_2$ or $Q_4$ is activated hydrocarbyloxy then the reaction is preferably carried out in an inert polar solvent, such as dimethylformamide. It is also preferred that the activated hydrocarbyloxy group is a pentachorophenyl ester and that the reaction is carried out an ambient temperature.

If a group $Q_2$ is labile acyloxy, reaction conditions are preferably as for $Q_1$, $Q_2$, or $Q_4$ halide hereinbefore.

When $Q_1$ and $Q_2$ together are O, the reaction is preferably carried out by heating a mixture of the reactants in an inert solvent to superatmospheric pressure in a pressurised container.

When $R_{16}$ is $(CH_2)_vCR_{17}R_{18}Q_2$ as hereinbefore defined, coupling with elimination of both $HQ_1$ and $HQ_2$ or $H(Q_1Q_2)H$ occurs under the reaction conditions described hereinbefore. Thus where $R_{17}$ and $R_{18}$ are each H, the resulting compound is of formula (I). When $R_{17}$ and $R_{18}$ together are oxo, the resulting compound must be reduced to be of formula (I). The reduction of the oxo group in the prepared compound is preferably carried out, with or without isolation of the compound by hydrogenation with tin/hydrochloric acid at an elevated temperature.

The invention also provides a second process for the preparation of a compound of formula (I) wherein A is of formula (III) wherein the variables are as hereinbefore defined, which process comprises reacting a compound of formula (IX)

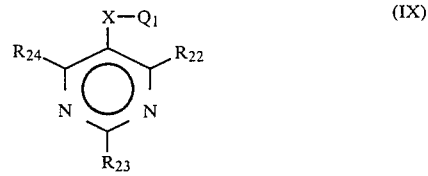

wherein
X is CO and $Q_1$ is a group displaceable by a nucleophile, or X is NH and $Q_1$ is H; and
$R_{22}$, $R_{23}$ and $R_{24}$ are as defined in relation to formula (III)
with a compound of formula (VIII) depicted hereinbefore, wherein
(i) when $Q_1$ in the compound of formula (IX) is a group displaceable by a nucleophile, $Q_3$ is $NH_2$;
(ii) when $Q_1$ in the compound of formula (IX) is H, $Q_3$ is $COQ_4$ where $Q_4$ is a group displaceable by a nucleophile;
and optionally thereafter converting any B, $R_{23}$, $R_{23}$ or $R_{24}$ group to another B, $R_{22}$, $R_{23}$ or $R_{24}$ group respectively and optionally forming a pharmaceutically acceptable salt, quaternary derivative or N-oxide of the resultant compound of formula (I).

Examples of groups displaceable by a nucleophile are as described hereinbefore for such groups in relation to the process for the preparation of a compound of formula (I) wherein A is of formula (II).

Reaction conditions for this process are as described hereinbefore in relation to the process for the preparation of a compound of formula (I) wherein A is of formula (II).

Pharmaceutically acceptable salts, quaternary derivatives, and N-oxides of the compounds of this invention may be formed conventionally. The salts may be formed for example by reaction of the base compound of formula (I) with a pharmaceutically acceptable organic or inorganic acid.

N-oxides of the nitrogen atom of the bicyclic ring system are produced by reaction of a compound of formula (I) with an organic peracid, such as m-chloroperbenzoic acid in, for example, a chlorinated hydrocarbon solvent at below ambient temperature.

Quaternary derivatives may be prepared by reaction of a compound of the present invention with the appropriate alkyl, aryl or aralkyl, chloride, bromide or iodide. This reaction may be carried out in a solvent, such as acetone, methanol, ethanol, dimethylformamide, at ambient or elevated temperature with or without pressure.

It will be apparent that compounds of the formula (I) containing an $R_1$, $R_2$, $R_3$, $R_4$, B, $R_{22}$, $R_{23}$ or $R_{24}$ group which is convertible to another $R_1$, $R_2$, $R_3$, $R_4$, B, $R_{22}$, $R_{23}$ or $R_{24}$ group are useful novel intermediates. A number of such conversions is possible not only for the end compounds of formula (I), but also for their intermediates as follows:

(a) a hydrogen substituent is convertible to a nitro substituent by nitration;
(b) a nitro substituent is convertible to an amino substituent by reduction;
(c) a $C_{1-7}$ carboxylic acylamino substituent is convertible to an amino substituent by deacylation;
(d) an amino substituent is convertible to a carboxylic $C_{1-4}$ acylamino substituent by acylation with a carboxylic acid derivative;
(e) a hydrogen substituent is convertible to a halogen substituent by halogenation;
(f) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;
(g) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene, by N-alkylation;
(h) an amino substituent is convertible to a $C_{1-6}$ alkylsulphonylamino group or an aminosulphonylamino group optionally N-substituted as defined by acylation with a $C_{1-6}$ alkylsulphonic acid or optionally N-substituted carbamic acid derivative;
(i) A $C_{1-4}$ alkylamino substituent group is convertible to a N-($C_{1-6}$ alkylsulphonyl)N-$C_{1-4}$ alkylamino group or an N-(amino sulphonyl)N-$C_{1-4}$ alkylamino group optionally N-substituted as defined by acylation with a $C_{1-6}$ alkylsulphonic acid or optionally N-substituted carbamic acid derivative.

Conversions (a) to (i) arre only exemplary and are not exhaustive of the possibilities.

In regard to (a), nitration is carried out in accordance with known procedures.

In regard to (b), the reaction is carried out with a reagent suitable for reducing nitroanisole to aminoanisole.

In regard to (c), deacylation is carried out by treatment with a base, such as an alkali metal hydroxide.

In regard to (d), (h), and (i) the acylation is carried out with an acylating agent, such as the corresponding acid or acid chloride. Formylation is carried out with the free acid.

In regard to (e), halogenation is carried out with conventional halogenating agents.

In regard to (f), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N-B moiety and suitable precautions will routinely be taken by the skilled man.

In regard to (g), alkylation is carried out with a corresponding alkylating agent such as the chloride or bromide under conventional conditions.

B optionally substituted benzyl as hereinbefore defined may be replaced by other B. Such B benzyl groups may, for example, be removed, when $R_1$, $R_2$, or $R_4$ is not halogen, by conventional transition metal catalysed hydrogenolysis to give compounds of the formula (X):

wherein the variables are as defined in formula (I).

This invention also provides a third process for the preparation of a compound of the formula (I) which comprises N-alkylating a compound of formula (X), and optionally forming a pharmaceutically acceptable salt, quaternary derivative or N-oxide of the resulting compound of the formula (I).

In this third process of the invention 'N-alkylation' comprises the substitution of the N-atom depicted in formula (X) by any group B as hereinbefore defined. This may be achieved by reaction of the compound of formula (X) with a compound $BQ_5$ wherein B is as hereinbefore defined and $Q_5$ is a leaving group.

Suitable values for $Q_5$ include groups displaced by nucleophiles such as Cl, Br, I, $OSO_2CH_3$ or $OSO_2C_6H_4CH_3$.

Favored values for $Q_5$ include Cl, Br and I. The reaction may be carried out under conventional alkylation conditions for example in an inert solvent such as dimethylformamide in the presence of an acid acceptor such as potassium carbonate. Generally the reaction is carried out an non-extreme temperature such as at ambient or slightly above.

Alternatively, 'N-alkylation' may be effected under conventional reductive alkylation conditions when the group B in the compound of formula (I) contains a methylene group adjacent to the N-atom in the bicycle.

Suitable reagents and conditions for such reductive alkylation are as described hereinafter for the preparation of compounds of the formula (IX). Suitable conditions are of course those illustrated by the Descriptions hereinafter for these compounds of the formula (IX).

Interconverting B in the compound of the formula (VIII) before coupling with the compound of the formula (VII) or (IX) is also possible. Such interconversions are effected conveniently under the above conditions. It is desirable to protect any amine function with a group readily removable by acidolysis such as a $C_{2-7}$ alkanoyl group, before B interconversion.

The substituents in the phenyl ring when B is benzyl in a compound of formula (I), in particular the substituted $C_{1-4}$ alkyl substituents, are interconvertible. A number of such interconversions are possible not only for the end compounds of formula (I), but also for their intermediates as follows:

(i) a carboxy $C_{1-4}$ alkyl substituent is convertible to an esterified carboxy $C_{1-4}$ alkyl substituent by esterification;

(ii) an esterified carboxy $C_{1-4}$ alkyl substituent is convertible to a carboxy $C_{1-4}$ alkyl subtituent by de-esterification;

(iii) an $C_{1-4}$ alkoxy $C_{1-4}$ alkyl substituent or an in vivo hydrolysable $C_{2-4}$ acyloxy $C_{1-4}$ alkyl substituent is convertible to an hydroxy $C_{1-4}$ alkyl substituent by de-etherification;

(iv) an optionally esterified carboxy or carboxy $C_{1-3}$ alkyl substituent is convertible to an hydroxymethyl or hydroxy $C_{2-4}$ substituent by reduction; and (v) a hydroxy $C_{1-4}$ alkyl substituent is convertible to $C_{1-4}$ alkoxy $C_{1-4}$ alkyl by O-alkylation or to in vivo hydrolysable $C_{1-4}$ acyloxy $C_{1-4}$ alkyl by O-acylation.

Conversions (i) to (v) are only exemplary and are not exhaustive of the possibilities.

In regard to (i) and (ii), the esterification and desterification reactions are carried out in conventional manner.

In regard to (iii), a $C_{1-4}$ alkoxy $C_{1-4}$ alkyl substituent is convertible to an hydroxy $C_{1-4}$ alkyl substituent by conventional methods, such as warming with aqueous hydrobromic acid or by treatment with pyridine hydrochloride, boron tribromide, boron triiodide or idodotrimethylsilane.

An in vivo hydrolysable $C_{2-4}$ acyloxy $C_{1-4}$ alkyl substituent is convertible to an hydroxy $C_{1-4}$ alkyl substituent by acid or base hydrolysis.

In regard to (iv), the reduction is carried out with a selective metal complex hydride, for example lithium aluminium hydride, under conventional conditions.

In regard to (v), O-alkylation is carried out under conventional conditions in an inert solvent at a non-extreme temperature such as ambient temperature or slightly above or at reflux temperature. The $C_{1-4}$ alkylating agent has a leaving group that is readily displaceable by a nucleophile. Examples of leaving groups include halide, such as chloride, bromide or iodide, or labile acyloxy groups, such as mesyl and tosyl.

O-acylation is carried out under conventional conditions with an acylating agent which has an acyl group capable of forming an in vivo hydrolysable acyloxy group and leaving group, such as halide, for example chloride and bromide, and hydrogen. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

Compounds of the formula (VIII) wherein $O_3$ is $NH_2$ or (X) are believed to be novel intermediates and thus form an aspect of the present invention.

When B in the compound of formula (VIII) wherein Q is $NH_2$ contains a methylene group adjacent to the N-atom in the bicycle it is ofen convenient in the preparation of such a compound of formula (VIII) to prepare the corresponding compound wherein the methylene group is replaced by —CO—, or for B methyl, where the methyl group is replaced by esterified carboxyl. Such compounds may then be reduced using a strong reductant such as lithium aluminium hydride to the corresponding compound of formula (VIII). The foregoing ring N-acyl compounds are also believed to be novel intermediates and as such form an aspect of the present invention.

Discussion hereinafter of the preparation of corresponding intermediates of formula (VIII) is to be taken as including the precaution of the corresponding N-acyl compounds as appropriate.

The compounds of formula (VII), or (IX) are known or are preparable analogously to, or routinely from, known compounds.

As mentioned hereinbefore the compounds of formula (I) exist in a number of stereoisomeric forms, in particular the moiety A can be in the $\alpha$ or the $\beta$ orientation to the bicyclic ring system. A mixture of such isomers can be obtained by a non-stereospecific process and then the desired isomer separated conventionally from the mixture by, for example, chromatography.

Compounds of the formula (VIII) wherein $Q_3$ is $NH_2$, or their ring N-acyl analogues as appropriate as discussed hereinbefore, may be prepared non-stereospecifically from known compounds by the processes illustrated in the Descriptions hereinafter.

Compounds of the formula (VIII) wherein $Q_3$ is $COQ^1_4$ where $Q^1_4$ is a group readily displaceable by a nucleophile and is other than hydroxy or their N-acyl analogues as appropriate as discussed hereinbefore are preparable conventionally from the corresponding compound wherein $Q_3$ is COOH.

These acids in turn may be prepared conventionally from the corresponding compounds wherein $Q_3$ is replaced by OH, as illustrated by the compounds of Description 2. This may be effected by conventional conversion of the OH group to a nitrile group or a lithium atom, followed by conventional conversion of the nitrile group or lithium atom to a carboxyl group.

The compounds of the present invention are dopamine antagonists and may generally be used in the treatment of emesis. Depending on their balance between peripheral and central action on the nervous system, they may also be used in the treatment of disorders related to impaired gatro-intestinal motility, such as retarded gastric emptying, dyspepsia, flatulence, esophagal reflux and peptic ulcer and/or in the treatment of disorders of the central nervous system, such as psychosis.

The invention also provides a pharmaceutical composition comprising a compound of the present invention, in particular a compound of formula (I), or a pharmaceutically acceptable salt, quaternary derivative or N-oxide thereof, or a pharmaceutically acceptable solvate or any of the foregoing and a pharmaceutically acceptable carrier.

Such compositions are prepared by admixture and are suitably adapted for oral or parental administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling, tabletting or the like. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of emesis or disorders of the central nervous system in mammals, such as humans, which comprises the administration of an effective amount of a compound of the present invention, or a pharmaceutically acceptable acid addition salt thereof, or a pharmaceutically acceptable solvate of either of the foregoing.

The invention further provides a method of treatment or prophylaxis of disorders related to impaired gastrointestinal motility in mammals, such as humans, which comprises the administration of an effective amount of a compound of the present invention, or a pharmaceutically acceptable salt, quaternary derivative or N-oxide thereof, or a pharmaceutically acceptable solvate of any of the foregoing.

An amount effective to treat the disorders hereinbefore described depends on the relative efficacies of the compounds of the invention, the nature and severity of the disorder being treated and the weight of the mammal. However, a unit dose will normally contain 0.1 to 200 mg for example 0.5 to 100 mg, of the compound of the invention. Unit doses will normally be administered more than once a day, for example, 2, 3, 4, 5, or 6 times a day such that the total daily dose is normally in the range 0.015 to 175 mg/kg per day, for example 0.075 to 90 mg/kg per day.

The compounds of the present invention have the ability to potentiate the effect of conventional analgesics in migraine treatment when administered concomitantly with the analgesic. Accordingly, the present invention also provides a pharmaceutical composition comprising a compound of the present invention and an analgesic. The effective amount of each component of the composition will depend in the usual way on a number of factors such as the nature and severity of the malady to be treated, the weight of the sufferer, and the actual compound used. However, the compound of the present invention and the analgesic, such as aspirin or paracetamol, are present in unit doses of the composition in amounts generally similar to their usual effective dose.

The composition can be a combination product, for example a tablet or capsule containing both a compound of the invention and an analgesic for oral administration, or a twin pack comprising the two active ingredients made up for separate administration.

The invention accordingly provides a method of treatment of migraine comprising the administration of an effective amount of a compound of the invention and an analgesic.

The invention provides a compound of the present invention or a pharmaceutically acceptable acid addition salt thereof, or a pharmaceutically acceptable solvate of either of the foregoing for the treatment or prophylaxis of emesis, disorders related to impaired gastro-intestinal motility or of the central nervous system.

The invention also provides a quaternary derivative or N-oxide of a compound of the present invention or a pharmaceutically acceptable solvate of either of the foregoing for the treatment or prophylaxis of disorders related to impaired gastro-intestinal motility.

The following Examples illustrate the preparation of compounds of formula (I). The following Descriptions illustrate the preparation of intermediates thereto.

In the Descriptions and Examples all compounds are prepared as their racemates, although only one enantiomer is depicted.

DESCRIPTION 1

(a) 2-Benzoyl-2-azabicyclo[2,2,2]oct-5-ene (D1a) intermediate for compounds (3), (4), (5), (6), (7), (8), (19), (20), (29), (30), (35), (36), (37), (38)

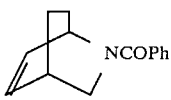
(D1a)

To a solution of 2-azabicyclo[2,2,2]-oct-5-ene (M. P. Cava et al, J. Org. Chem., 30, 3772 (1965)) (3.3 g) in aqueous 2.5N sodium hydroxide (50 ml) was added benzoyl chloride (6 ml) and the mixture stirred vigourously for 1 hour. Extraction into ether (2×100 ml), drying (Na₂SO₄) and concentration afforded the 2-benzoyl-2-azabicyclo[2,2,2]oct-5-ene (D1a) (3.7 g, 55%).

Following the procedure outlined above, the following olefins are prepared.

(b) 2-Trimethylacetyl-2-azabicyclo[2,2,2]oct-5-ene (D1b) intermediate for compounds (9), (10), (21), (22)

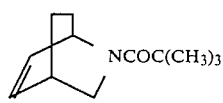
(D1b)

(c) 2-m-chlorobenzoyl-2-azabicyclo[2,2,2]oct-5-ene (D1c) intermediate for compounds (11), (12), (23), (24)

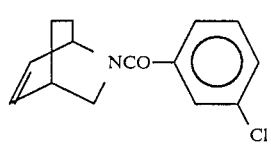
(D1c)

(d) 2-Carbethoxy-2-azabicyclo[2,2,1]hept-5-ene (D1d) intermediate for compounds (13), (14), (25), (26), (33), (34)

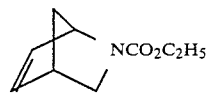
(D1d)

(e) 2-Benzoyl-2-azabicyclo[2,2,1]hept-5-ene (D1e) intermediate for compounds (15), (16), (27), (28)

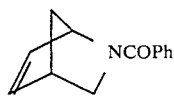
(D1e)

DESCRIPTION 2

(a) (±)-5-Hydroxy-2-benzoyl-2-azabicyclo[2,2,2]octane (D2a) intermediate for compounds (3) to (8), (19), (20), (29), (30), (35), (36), (37), (38)

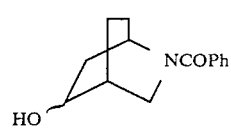
(D2a)

This compound was prepared from the 2-benzoyl-2-azabicyclo[2,2,2]oct-5-ene (D1a) (5.7 g) via oxymercuration and reduction as described by G. Krow et al (Syn. Commun. 2(4), 211 (1972)) (5.0 g, 80%). m.s. M⁺ 231.1252 (Theory 231.1258).

Following the procedure outlined above, the following alcohols were prepared:

(b) (±)-5-Hydroxy-2-trimethylacetyl-2-azabicyclo[2,2,2]octane (D2b) intermediate for compounds (9), (10), (21), (22)

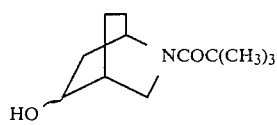
(D2b)

(c) (±)-5-Hydroxy-2-m-chlorophenyl-2-azabicyclo[2,2,2]octane (D2c) intermediate for compounds (11), (12), (23), (24)

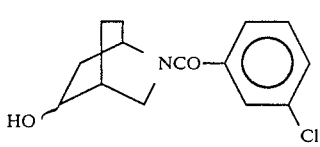
(D2c)

(d)
(±)-5-Hydroxy-2-carbethoxy-2-azabicyclo[2,2,1]heptane (D2d) intermediate for compounds (13), (14), (25), (26), (33), (34)

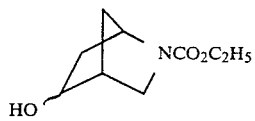
(D2d)

(e)
(±)-5-Hydroxy-2-benzoyl-2-azabicyclo[2,2,1]heptane (D2c) intermediate for compounds (15), (16), (27), (28)

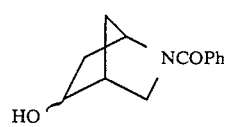
(D2e)

DESCRIPTION 3

(a)
(±)-5-Azido-2-carbethoxy-2-azabicyclo[2,2,2]octane (D3a) intermediate for compounds (1), (2), (17), (18), (31), (32)

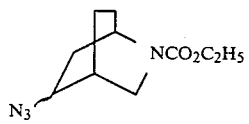
(D3a)

To a stirred solution of (±) 5-hydroxy-2-carbethoxy-2-azabicyclo-[2,2,2]octane (2 g) prepared as described by G. Krow et al (Syn. Commun. 2(4), 211 (1972)) and triethylamine (2 ml) in methylene chloride (100 ml) at 0° C. was added a solution of mesylchloride (1.0 ml) in CH$_2$Cl$_2$ (10 ml), and the solution was stirred to room temperature over 1 hr. After washing (Na$_2$CO$_3$ soln) and drying (Na$_2$SO$_4$), the methylene chloride was evaporated to give the crude mesylate (2.8 g). This was dissolved in N-methylpyrrolidinone (50 ml) and heated to 150° for 1 hr with sodium azide (1.5 g). On cooling, water (200 ml) was added and the product extracted into ether/petrol (2:1), washed with water (2×100 ml) and dried (Na$_2$SO$_4$). Concentration afforded the crude (±) 5-azido-2-carbethoxy-2-azabicyclo[2,2,2]octane (D3a) (1.4 g, 65%).

Following the procedure outlined above, the following azide was prepared.

(b) (±)-5-Azido-2-benzoyl-2-azabicyclo[2,2,2]octane (D3b), (85%), intermediate for compounds (3) to (8), (19), (20), (29), (30), (35), (36), (37), (38)

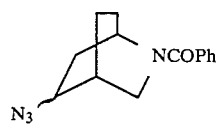
(D3b)

Following the above procedure the following azides are prepared.

(c)
(±)-5-Azido-2-trimethylacetyl-2-azabicyclo-[2,2,2]octane (D3c) intermediate for compounds (9), (10), (21), (22)

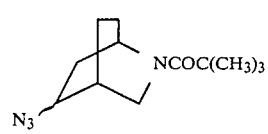
(D3c)

(d)
(±)-5-Azido-2-m-chlorobenzoyl-2-azabicyclo[2,2,2]octane (D3d) intermediate for compounds (11), (12), (23), (24)

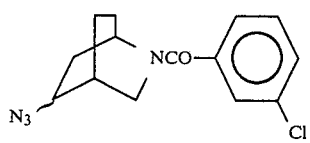
(D3d)

(e)
(±)-5-Azido-2-carbethoxy-2-azabicyclo[2,2,1]heptane (D3e) intermediate for compounds (13), (14), (25), (26), (33), (34)

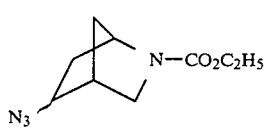
(D3e)

(f) (±)-5-Azido-2-benzoyl-2-azabicyclo[2,2,1]heptane (D3f) intermediate for compounds (15), (16), (27), (28)

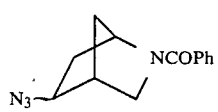
(D3f)

DESCRIPTION 4

(a) (±)-5-Amino-2-methyl-2-azabicyclo[2,2,2]octane (D4a) intermediate for compounds (1), (2), (17), (18), (31), (32)

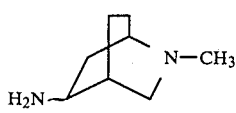
(D4a)

To a stirred suspension of LiAlH$_4$ (2 g) in dry THF (100 was added a solution of the (±)-5-azido-2-carbethoxy-2-azabicyclo[2,2,2]octane (D3a) (3.5 g) under dry nitrogen and the mixture heated under reflux for 5 hrs. Normal basic work-up afforded the crude (±) 5-amino-2-methyl-2-azabicyclo[2,2,2]octane (D4a) (1.6 g, 70%), purified by distillation (b.p. 75°/5 mmHg).

Following the procedure outlined above, the following amines are prepared:

(b) (±)-5-Amino-2-neopentyl-2-azabicyclo[2,2,2]octane (D4b), intermediate for compounds (9), (10), (21), (22)

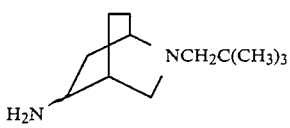
(D4b)

(c) (±)-5-Amino-2-methyl-2-azabicyclo[2,2,1]heptane (D4c) intermediate for compounds (13), (14), (25), (26), (33), (34)

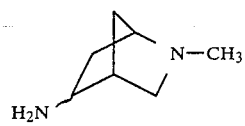
(D4c)

(d) (±)-5-Amino-2-benzyl-2-azabicyclo[2,2,2]octane (D4d) intermediate for compounds (3) to (8), (19), (20), (29), (30), (35), (36), (37), (38)

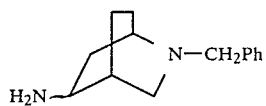
(D4d)

To a stirred solution of (±) 5-azido-2-benzoyl-2-azabicyclo[2,2,2]octane (D3d) (3.3 g) in dry THF (100 ml) under nitrogen was added a solution of diborane in THF (50 ml, 1M solution) and the whole heated under reflux for 12 hours. On cooling, an excess of 5N HCl was added and the mixture heated on a steam bath for 2 hrs. Basification and saturation with $K_2CO_3$, extraction with $CH_2Cl_2$, drying ($K_2CO_3$), concentration and distillation afforded the (±)-5-amino-2-benzyl-2-azabicyclo[2,2,2]-octane (D4b) (2.7 g, 85%) bp 120°–140°/0.1 mm.

Following the procedures outlined above, the following amines are prepared.

(e) (±)-5-Amino-2-m-chlorobenzyl-2-azabicyclo-[2,2,2]octane (D4e), intermediate for compounds (11), (12), (23), (24)

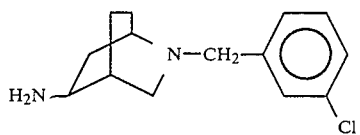
(D4e)

(f) (±)-5-Amino-2-benzyl-2-azabicyclo[2,2,1]heptane (D4f) intermediate for compounds (15), (16), (27), (28)

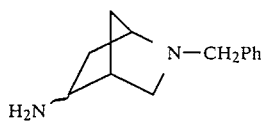
(D4f)

As noted hereinbefore, the moiety A in the compounds of formula (I) may be in either of two orientations at its point of attachment to the bicyclic ring system, giving rise to two stereoisomers. Reaction of any of the intermediates (D4a) to (D4f) described hereinbefore to give a compound of formula (I) will give both such isomers of the compound of formula (I).

Any compound described hereinafter as Isomer 1 has the same stereochemistry at the point of attachment of the moiety A to the bicycle as that of of Compound (1) hereinafter. Any described as Isomer 2 has the stereochemistry of Compound (2).

Any compound of formula (I) with the stereochemistry of Isomer 1 (i.e. that of Compound 1) is described herein as 'axial'. Any compound of formula (I) with the stereochemistry of Isomer 2 (i.e that of Compound 2) is described herein as 'equatorial'.

In Example 3, any compound described as the less polar isomer has the stereochemistry of Compound (1). Any compound described as the more polar isomer has the stereochemistry of Compound (2).

EXAMPLE 1

Compounds (1) and (2)

(±)-4-Acetamido-5-chloro-2-methoxy-N-(5-[2-methyl-2-aza-bicyclo[2,2,2]octyl])benzamide, Isomers (1) and (2)

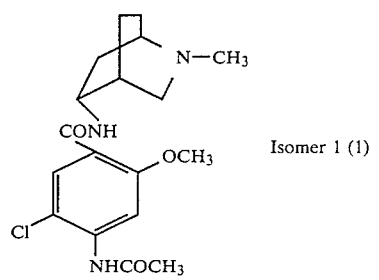
Isomer 1 (1)

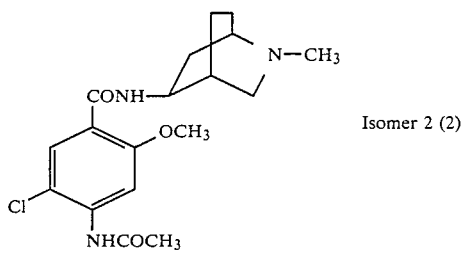
Isomer 2 (2)

To a stirred solution of 4-acetamido-5-chloro-2-methoxybenzoyl chloride (4.7 g) in dry methylene chloride (200 ml) was added triethylamine (6 ml) and (D4a) (2.3 g). After stirring for 4 hours, 2.5N sodium hydroxide solution (25 ml) was added, and the organic layer separated, dried ($K_2CO_3$) and concentrated. Column chromatography (TLC) silica, under pressure 5:1 loading) afforded (i) 5% $MeOH/CHCl_3$: Isomer 1 of (±)-4-acetamido-5-chloro-2-methoxy-N-(5-[2-methyl-2-azabicyclo[2,2,2]octyl])benzamide (1) (2.6 g)

n.m.r. (δ, $CDCl_3$) 8.5–7.7 (m, 4H, $ArCON\underline{H}$, $CH_3CON\underline{H}$ including 8.10, s, and 7.97, s, both 1H, aromatic $\underline{H}$): 4.4–3.4 (m, 5H, including 3.85, s, 3H, $OC\underline{H}_3$) 3.3–2.9 (brd, 1H, aliphatic $\underline{H}$) 2.8–1.1 (m, 14H, aliphatic $\underline{H}$ including 2.41, s, 3H, $NC\underline{H}_3$ and 2.21, s, 3H, $COC\underline{H}_3$).

m.s. M+ 365.1489 (theory 365.1504).

(ii) 10% MeOH/CHCl₃: Isomer 2 of (±)-4-acetamido-5-chloro-2-methoxy-N-(5-[2-methyl-2-azabicyclo[2,2,2]octyl])benzamide (2) (3.1 g)

n.m.r. (δ, CDCl₃): 8.3–7.4 (m, 4H, ArCONH, CH₃CONH including 8.17, s and 8.03, s, both 1H, aromatic H) 4.5–3.5 (m, 4H, including 3.90, s, 3H, OCH₃) 3.1–1.0 (m, 16H, aliphatic H including 2.50, s, 3H, NCH₃ and 2.23, s, 3H, COCH₃).

m.s. M+ 365.1489 (Theory 365.1504).

The following were prepared analogously:

COMPOUND 3

(±) 4-Acetamido-5-chloro-2-methoxy-N-(5-[2-benzyl-2-azabicyclo[2,2,2]octyl)benzamide (Isomer 1)

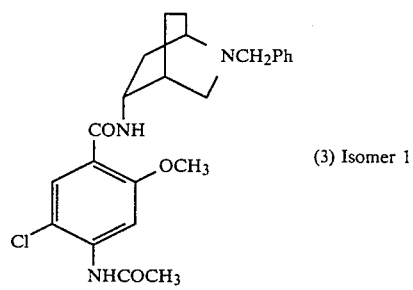

(3) Isomer 1 n.m.r. (δ, CDCl₃) 8.5–7.6 (m, 4H, ArCONH, CH₃CONH including 8.20, s, and 8.10, s, both 1H, aromatic H) 7.5–6.9 (m, 5H, aromatic H) 4.5–3.3 (m, 6H, aliphatic H including 3.84, s, 3H, OCH₃ and 3.61, s, 2H, aryl CH₂) 3.2–1.0 (m, 13H, remaining protons including 2.22, s, 3H, COCH₃).

COMPOUND 4

(±)-4-Acetamido-5-chloro-2-methoxy-N-(5-[2-benzyl-2-azabicyclo[2,2,2]octyl])benzamide (Isomer 2)

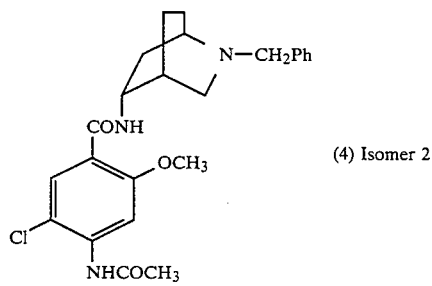

(4) Isomer 2 n.m.r. (δ, CDCl₃) 8.3–7.4 (m, 4H, ArCONH CH₂CONH including 8.08, s, 7.98, s, both 1H, aromatic H) 7.5–6.9 (m, 5H, aromatic H) 4.5–3.5 (m, 6H, aliphatic H including 3.85, s, 3H, OCH₃ and 3.69, s, 2H, aryl —CH₂—) 2.9–1.0 (m, 13H, remaining protons including 2.21, s, 3H, COCH₃)

The following are prepared analogously:

COMPOUNDS (5) AND (6)

2-methoxy-5-dimethylaminosulphonylbenzoyl chloride is reacted with the primary amine produced in Description 4d to give, after isomer separation, Isomer 1 (5) and Isomer 2 (6) of a compound of formula:

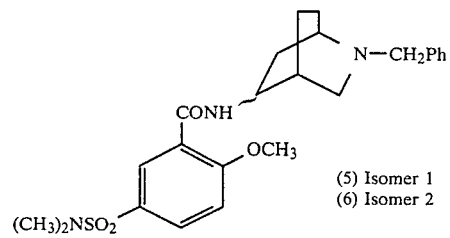

(5) Isomer 1
(6) Isomer 2 as their racemates.

COMPOUNDS (7) AND (8)

2,3-Dimethoxybenzoyl chloride is reacted with the primary amine produced in Description 4d to give, after isomer separation, Isomer 1 (7) and Isomer 2 (8) of a compound of formula:

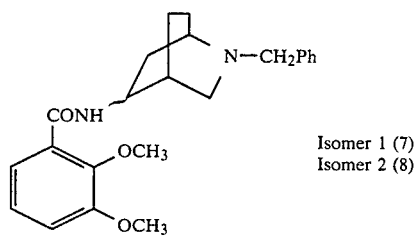

Isomer 1 (7)
Isomer 2 (8)

as their racemates.

COMPOUNDS (9) AND (10)

Isomer 1 (9) and Isomer 2 (10) of a compound of formula:

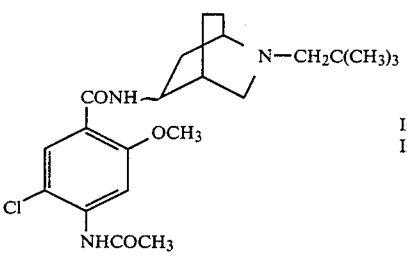

Isomer 1 (9)
Isomer 2 (10)

as their racemates.

COMPOUNDS (11) AND (12)

Isomer 1 (11) and Isomer 2 (12) of a compound of formula:

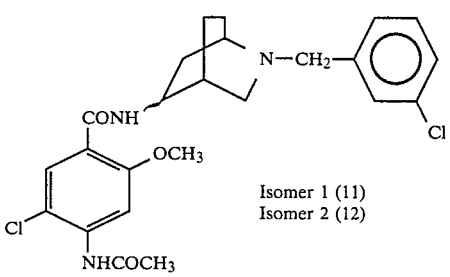

Isomer 1 (11)
Isomer 2 (12)

as their racemates

EXAMPLES (13) AND (14)

Isomer 1 (13) and Isomer 2 (14) of a compound of formula:

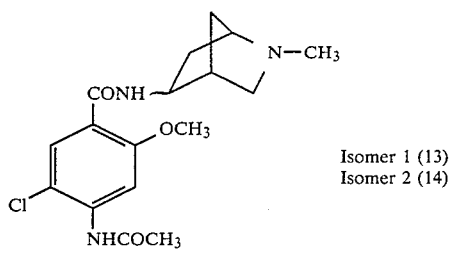

Isomer 1 (13)
Isomer 2 (14)

as their racemates.

EXAMPLES (15) AND (16)

Isomer 1 (15) and Isomer 2 (16) of a compound of formula:

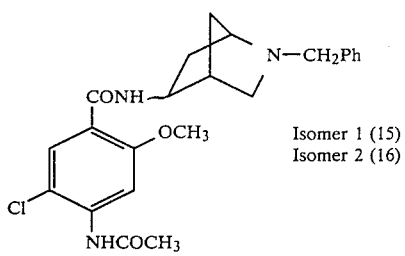

Isomer 1 (15)
Isomer 2 (16)

as their racemates.

EXAMPLE 2

COMPOUND (17)

(±)-4-Amino-5-chloro-2-methoxy-N-(5-[2-methyl-2-azabicyclo[2,2,2]octyl]benzamide (Isomer 1)

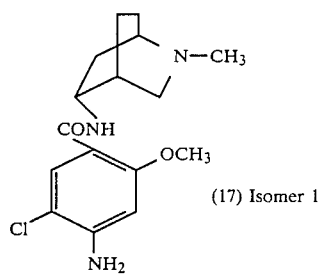

(17) Isomer 1

(1) (2.6 g) (Prepared as in Example 1) was heated under reflux in ethanol (50 ml) with aqueous sodium hydroxide (2.5N, 15 ml) for 2 hrs. On cooling and concentration, water (100 ml) was added and the oil extracted with ethyl acetate (2×100 ml). Drying (Na$_2$SO$_4$), concentration and recrystallisation (ethylacetate/petrol) gave the (±)-4-amino-5-chloro-2-methoxy-N-(5-[2-methyl-2-azabicyclo[2,2,2]octyl]) benzamide (Isomer 1) (17) (1.8 g) m.p. 197°–9° n.m.r. (δ, CDCl$_3$) 8.2–7.8 (m, 2H, CONH including 8.07, s, 1H, aryl 6H) 6.29 (s, 1H, aryl 3H) 4.7–3.7 (m, 7H, aryl NH$_2$, aliphatic H, including 3.88, s, 3H, OCH$_3$). 3.1–2.8 (br.d, 1H, aliphatic H) 2.75–1.1 (m, 11H, aliphatic H including 2.35, s, 3H, NCH$_3$)

m.s. M+ 323.1397 (Theory 323.1398).

COMPOUND (18)

(±)

4-Amino-5-chloro-2-methoxy-N-(5-[2-methyl-2-azabicyclo[2,2,2]octyl]benzamide (Isomer 2)

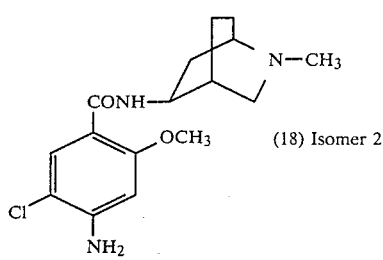

(18) Isomer 2

Following the procedure outlined above (2) (3.1 g) was converted into (±)-4-amino-5-chloro-2-methoxy-N-(5-[2-methyl-2-azabicyclo[2,2,2]octyl]-benzamide (Isomer 2) (18) isolated as its monohydrochloride (18A) (1.8 g) (m.p. 154°–6°).

n.m.r. (δ, d$^6$DMSO) 7.95–7.75 (br.d, H, CONH) 7.58 (s, 1H, aryl 6H) 6.50 (s, 1H, aryl 3H) 5.92 (brs, 2H, aryl —NH$_2$) 4.4–3.7 (m, 5H, including 3.61, s, 3H, OCH$_3$) 3.4–3.0 (m, 2H, aliphatic H) 2.74 (s, 3H, NCH$_3$) 2.2–1.3 (m, 7H, aliphatic H)

m.s. M+ (free base) 323.1414 (Theory 323.1398).

(These data are for (18A)).

The following were prepared analogously.

COMPOUND (19)

(±)-4-Amino-5-chloro-2-methoxy-N-(5-[2-benzyl-2-azabicyclo[2,2,2]octyl]benzamide (Isomer 1)

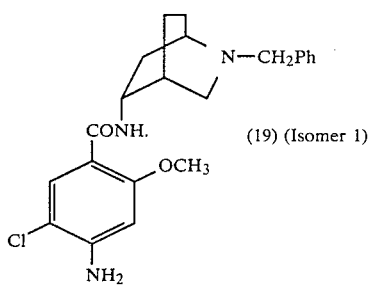

(19) (Isomer 1)

n.m.r. (δ, CDCl$_3$) 8.3–8.0 (m, 2H, CONH, including 8.09, s, 1H, aryl 6H) 7.5–7.1 (m, 5H, aryl H) 6.29 (s, 1H, aryl 3H) 4.6–4.1 (m, 3H, NH$_2$+aliphatic H) 3.80 (s, 3H, OCH$_3$) 3.65 (s, 2H, aryl —CH$_2$) 3.2–2.9 (br.d, 1H, aliphatic H) 2.75–2.55 (m, 1H, aliphatic H) 2.55–2.3 (br.d, 1H, aliphatic H) 2.2–1.2 (m, 7H, aliphatic H).

COMPOUND (20)

(±)
4-Amino-5-chloro-2-methoxy-N-(5-[2-benzyl-2-azabicyclo[2,2,2]octyl])benzamide (Isomer 2)

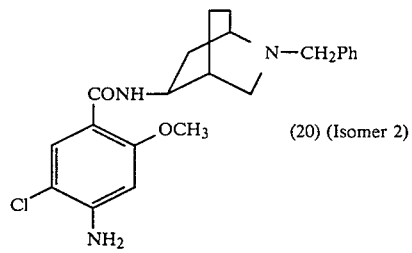

(20) (Isomer 2)

n.m.r. (δ CDCl$_3$) 8.08 (s, 1H, aryl 6$\underline{H}$) 8.0–7.7 (br.d, 1H, CON$\underline{H}$) 7.5–7.1 (m, 5H, aryl $\underline{H}$) 6.29 (s, 1H, aryl 3$\underline{H}$) 4.6–4.1 (m, 3H, N$\underline{H_2}$+aliphatic $\underline{H}$) 3.88 (s, 3H, OC$\underline{H_3}$) 3.65 (s, 2H, aryl $\underline{CH_2}$) 2.9–2.3 (m, 4H, aliphatic $\underline{H}$) 2.2–1.0 (m, 6H, aliphatic $\underline{H}$).

The following are prepared analogously:

COMPOUNDS (21) AND (22)

Isomer 1 (21) and Isomer 2 (22) of a compound of formula:

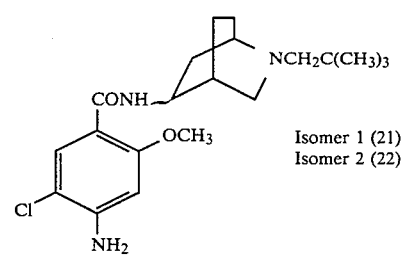

Isomer 1 (21)
Isomer 2 (22)

as their racemates.

COMPOUNDS (23) AND (24)

Isomer 1 (23) and Isomer 2 (24) of a compound of formula:

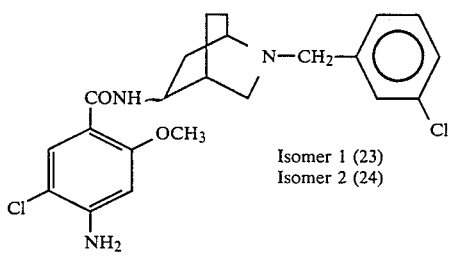

Isomer 1 (23)
Isomer 2 (24)

as their racemates.

COMPOUNDS (25) AND (26)

These compounds, which are prepared by the route of Example 2, were also prepared by the method of Example 3 hereinafter and are described and characterised therein.

Isomer 1 (25)
Isomer 2 (26)

as their racemates.

COMPOUNDS (27) AND (28)

Isomer 1 (27) and Isomer 2 (28) of a compound of formula:

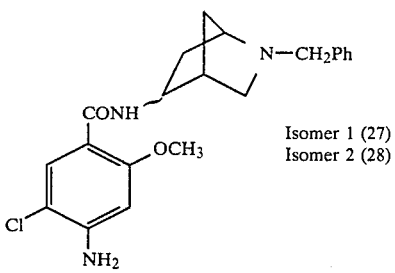

Isomer 1 (27)
Isomer 2 (28)

as their racemates.

EXAMPLE 3

Alternative Synthesis of compounds (17) and (18)

(±)
4-Amino-5-chloro-2-methoxy-N-[5-(2-methyl-2-azabicyclo(2.2.2)octyl)]benzamide

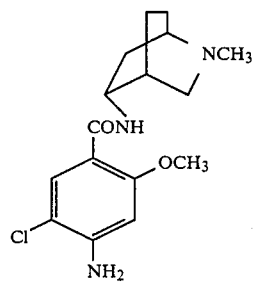

(17)

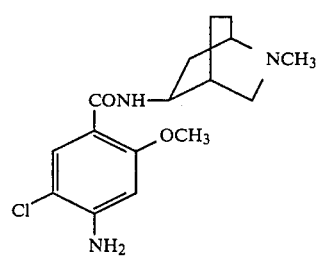

(18)

Ethyl chloroformate (8.13 g) in dry dichloromethane (50 ml) was added dropwise, over 30 minutes, to a suspension of 4-amino-5-chloro-2-methoxybenzoic acid (15.1 g) and triethylamine (7.58 g) in dry dichloromethane (700 ml), under nitrogen. After 15 minutes, 5-amino- 2-methyl-2-azabicyclo[2.2.2]octane (D4a) (10.5 g) in dry dichloromethane (50 ml) was added dropwise. The resultant solution was stirred, at room temperature, for about 2 hours. Sodium hydroxide solution (2.5N) was added and the mixture was stirred for about 30 minutes. The organic phase was washed with brine, dried (Na$_2$CO$_3$) and evaporated in vacuo to give an isomeric mixture of (17) and (18). This was triturated with ether then chromatographed on 5% deactivated alumina (20:1) using dichloromethane as eluant. This gave initially the less polar isomer (17) (3.97 g), identical to that previously prepared. This was converted into its hydrochloride salt mp 197°–9° C. (Compound (17A)).

Further elution gave the more polar isomer (18).

In a similar manner were prepared the isomers of 4-amino-2-methoxy-5-methylsulphonyl-N-[5-(2-benzyl-2-azabicyclo(2.2.2)octyl)]benzamide (29) and (30).

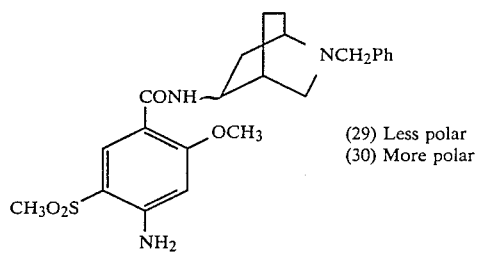

(29) Less polar
(30) More polar

Less polar (29) Mpt. 105°–108° C.

| ms | C$_{23}$H$_{29}$N$_3$O$_4$S | Theoretical Mass: | 443.1878 |
| | | Observed Mass: | 443.1877 |
| nmr (δCDCl$_3$) | 8.6 | (s, 1H, aryl 6H) | |
| | 8.0 | (bd, 1H, CONH) | |
| | 7.45–7.2 | (m, 5H, C$_6$H$_5$—) | |
| | 6.25 | (s, 1H, aryl 3H) | |
| | 5.5 | (bs, 2H, NH$_2$) | |
| | 4.45–4.1 | (m, 1H, CONH.C.H) | |
| | 4–1.25 | (m, 18H, aliphatic protons including 3.85, s, 3H, CH$_3$O and 3.65, s, 2H, CH$_2$Ph and 3.0, s, 3H, CH$_3$O$_2$S) | |

More polar (30) as its hemihydrate (30A) Mpt. 101°–105° C.

| ms | C$_{23}$H$_{29}$N$_3$O$_4$S. | Theoretical Mass: | 443.1878 |
| | | Observed Mass: | 443.1882 |

Analysis: C$_{23}$H$_{29}$N$_3$O$_4$S.½H$_2$O
| Requires: | C, 61.12; | H, 6.47; | N, 9.30; | S, 7.09% |
| Found: | 61.42; | 6.22; | 9.29; | 6.61% |

| nmr (δCDCl$_3$) | 8.55 | s, 1H, aryl 6H) |
| | 7.65 | (bd, 1H, CONH) |
| | 7.5–7.1 | (m, 5H, C$_6$H$_5$—) |
| | 6.25 | (s, 1H, aryl 3H) |
| | 5.5 | (bs, 2H, NH$_2$) |
| 4.5–4.15 | (m, 1H, CONH.C.H) |
| 3.95 | (s, 3H, OCH$_3$) |
| 3.65 | (s, 2H, CH$_2$Ph) |
| 3.1–1.0 | (m, 13H, aliphatic protons including 3.0, s, 3H, CH$_3$O$_2$S) |

These data are for (30A)

In a similar manner were prepared the isomers of (±) 2-methoxy-5-dimethylsulphamoyl-N-[5-(2-methyl-2-azabicyclo(2.2.2)octyl)]benzamide (31) and (32). (32) was converted to its hydrochloride salt (32A).

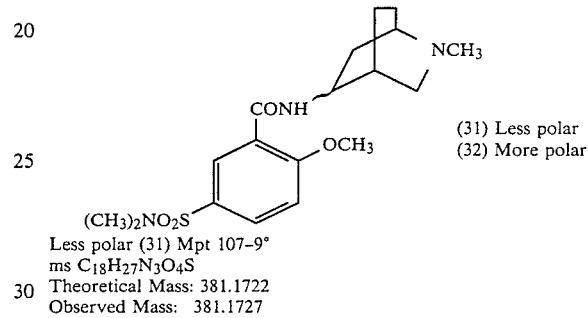

(31) Less polar
(32) More polar

Less polar (31) Mpt 107–9°
ms C$_{18}$H$_{27}$N$_3$O$_4$S
Theoretical Mass: 381.1722
Observed Mass: 381.1727

Analysis: C$_{18}$H$_{27}$N$_3$O$_4$S.

| Requires: | C, 56.67; | H, 7.13; | N, 11.01; | S, 8.39% |
| Found: | 56.47; | 7.25; | 10.95 | 8.24% |
| | 56.25; | 7.18; | 10.91; | 8.30% |

| nmr (δCDCl$_3$) | 8.6 | (d, 1H, aryl 6H) |
| | 8.15 | (bdm 1H, CONH) |
| | 7.9 | (dd, 1H, aryl 4H) |
| | 7.15 | (d, 1H aryl 3H) |
| | 4.5–3.9 | (m, 4H aliphatic 5H CONH.C.H) |
| | 3.25–1.1 | (m, 19H aliphatic protons including 4.1, s, 3H, OCH$_3$ including 2.65, s, 6H, (CH$_3$)$_2$NSO$_2$ and 2.4, s, 3H, NCH$_3$). |

Hydrochloride salt of more polar isomer (32A)

Mpt 211–13° C.
| ms | C$_{18}$H$_{27}$N$_3$O$_4$S | Theoretical Mass: | 381.1722 |
| | | Observed Mass: | 381.1719 |

| Analysis: | C$_{18}$H$_{28}$N$_3$O$_4$SCl |
| Requires: | C, 51.73; H, 6.75; N, 10.05; S, 7.67; Cl, 8.48 |
| Found: | C, 51.41; H, 6.81; N, 9.71; S, 7.01; Cl, 8.48 | nmr (δ(CD₃)₂SO) 8.30 (bd, 1H, CON$\underline{H}$); 7.95–7.7 (m, 2H, aryl 6$\underline{H}$+4$\underline{H}$); 7.35 (d, 1H, aryl 3$\underline{H}$); 4.4–1 (m, 23H, aliphatic protons including; 3.95, s, 3$\underline{H}$, OC$\underline{H}_3$ and 2.75, s, 3H, NC$\underline{H}_3$ and 2.6, s, 6H, (C$\underline{H}_3$)₂NSO₂).

In a similar manner were prepared the isomers of (±) 4-amino-5-chloro-2-methoxy-N-[5-(2-methyl-2-azabicyclo(2.2.1)heptyl)]benzamide (25) and (26). These were converted to their hydrochloride salts (25A) and (26A) respectively.

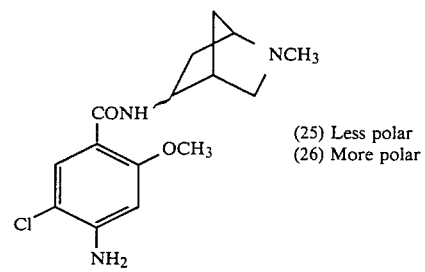

(25) Less polar
(26) More polar

Hydrochloride salt hydrate of less polar isomer (25A) Mpt 230°–5° C.

| ms | C₁₅H₂₀N₃O₂Cl | Theoretical mass: | 309.1244 |
| | | Observed mass: | 309.1245 |

| Analysis: | C₁₅H₂₀N₂O₂Cl.HCl.H₂O | | | |
| Required: | C, 49.46; | H, 6.36; | N, 11.54; | Cl, 19.47% |
| Found: | 49.95; | 6.05; | 11.56; | 19.86% |

| nmr | (δ(CD₃)₂SO) | |
| | 7.7 | (bd, 1H, CON$\underline{H}$) |
| | 7.6 | (s, 1H, aryl 6$\underline{H}$) |
| | 6.5 | (s, 1H, aryl 3$\underline{H}$) |
| | 5.95 | (bs, 2H, N$\underline{H}_2$) |
| | 4.5–4.3 | (m, 1H, CONH.$\underline{\text{C.H}}$) |
| | 3.8 | (s, 3H, OC$\underline{H}_3$) |
| | 4–2.9 | (m, 7H, aliphatic protons including 2.75, s, 3H, NC$\underline{H}_3$) |
| | 2.25–1.5 | (m, 4H aliphatic protons) |

Hydrochloride salt of more polar isomer (26A) Mpt 148°–51° C.

| ms | C₁₅H₂₀N₃O₂Cl | Theoretical Mass: | 309.1243 |
| | | Observed Mass: | 309.1238 | nmr (δ(CD₃)₂SO) 8.0 (bd, 1H, CON$\underline{H}$); 7.65 (s, 1H, aryl 6$\underline{H}$); 6.5 (s, 1H aryl 3$\underline{H}$); 5.95 (bs, 2$\underline{H}$, N$\underline{H}_2$); 4.5–4.2 (m, 1$\underline{H}$, CONH.C.$\underline{H}$); 3.9 (s, 3H, OC$\underline{H}_3$); 4–2.6 (m, 7H aliphatic protons including 2.7, s, 3$\underline{H}$, NC$\underline{H}_3$); 2.3–1.5 (m, 4H aliphatic protons).

In a similar manner were prepared the isomers of (±) 4-amino-2-methoxy-5-methylsulphonyl-N-[5-(2-methyl-2-azabicyclo(2.2.1)]heptylbenzamide (33) and (34) These were converted to their hydrochloride salts (33A) and (34A) respectively.

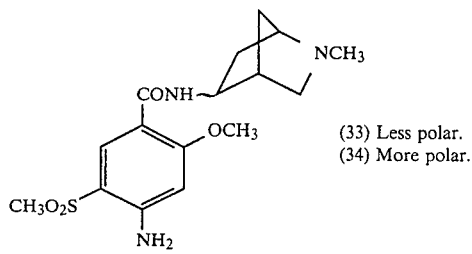

(33) Less polar.
(34) More polar.

Hydrochloride salt of less polar isomer (33A).

| ms | C₁₆H₂₃N₃O₄S | Theoretical Mass: | 353.1409 |
| | | Observed Mass: | 353.1407 |
| nmr | (δ(CD₃)₂SO) | | |
| | 8.05 | (s, 1H, aryl 6$\underline{H}$) | |
| | 7.75 | (bd, 1H, CON$\underline{H}$) | |
| | 6.6–6.4 | (bd, 3H, aryl 3$\underline{H}$ + N$\underline{H}_2$) | |
| | 4.6–4.3 | (m, 1H, CONH.$\underline{\text{C.H}}$) | |
| | 3.85 | (s, 3H, OC$\underline{H}_3$) | |
| | 3.9–2.4 | (m, 10H, aliphatic protons including 3.2, 3H, C$\underline{H}_3$O₂S and 2.55, 3H, NC$\underline{H}_3$) | |
| | 2.25–0.9 | (m, 4H, aliphatic protons) | |

Hydrochloride salt of more polar isomer (34A) Mpt 239°–41° C.

| ms | C₁₆H₂₂N₃O₄S | Theoretical Mass: | 353.1409 |
| | | Observed Mass: | 353.1421 |

| Analysis: | C₁₆H₂₄N₃O₄SCl | | | |
| Requires: | C, 49.29; | H, 6.2; | N, 10.77; | S, 8.22; |
| Found: | 49.38; | 6.3; | 10.71; | 8.35; |

| nmr (δ(CD₃)₂SO) | |
| 8.25–7.95 | (m, 2H, aryl 6$\underline{H}$, and CON$\underline{H}$) |
| 6.7–6.4 | (bd, 3H, aryl 3$\underline{H}$ and N$\underline{H}_2$) |
| 4.5–4.1 | (m, 1H, CONH.$\underline{\text{C.H}}$) |
| 4.1–1.1 | (m, 17H, aliphatic protons including 4.0, s, OC$\underline{H}_3$ and 3.1, s, C$\underline{H}_3$O₂S and 2.25, s, NC$\underline{H}_3$). |

The following are prepared analogously:

COMPOUNDS (35) AND (36)

The mixed anhydride formed between 2-methoxy-5-aminosulphonylbenzoic acid and ethyl chloroformate is reacted with the primary amine produced in Description 4d to give, after isomer separation, Isomer 1 (35) and Isomer 2 (36) of a compound of formula:

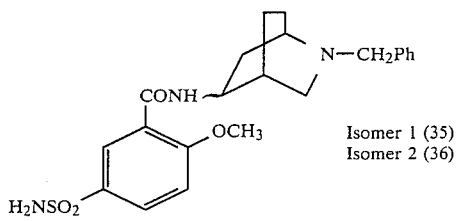

Isomer 1 (35)
Isomer 2 (36)

as their racemates.

COMPOUNDS (37) AND (38)

The mixed anhydride formed between 2-amino-4-methoxy-5-pyrimidyl carboxylic acid and ethyl chloroformate is reacted with the primary amine produced in Description 4d to give, after separation, Isomer 1 (37) and Isomer 2 (38) of a compound of formula:

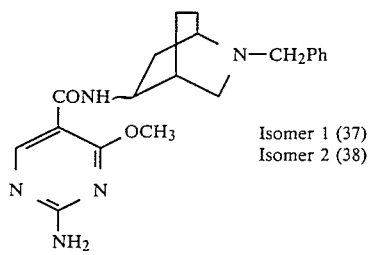

Isomer 1 (37)
Isomer 2 (38)

as their racemates.

PHARMACOLOGICAL DATA

Increase in intragastric pressure

Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre-dose period of 40 minutes was allowed to obtain a measure of spontaneous activity. An index of activity was obtained by measuring the average height of pressure waves during 10 minute periods. Values for 4 such periods were obtained during assessment of spontaneous activity and for a 40 minute period after administration of compound. Student's 't' test was applied to the difference in average values obtained for spontaneous and post compound activity.

Compounds (17), (18), (20) and (26) each significantly increased the index of activity post administration at a dose level of 0.5 mg/kg s.c. Compound (19) was similarly active at 1.0 mg/kg s.c.

ANTI-EMETIC ACTIVITY IN THE DOG

Compounds were administered subcutaneously 30 minutes prior to administration of a standard dose of apormorphine HCl (0.1 mg/kg subcutaneously) and the vomiting response compared to that obtained when the same animals were dosed with apomorphine HCl and vehicle only. The $ED_{50}$ value for inhibition of the vomiting response determined for compounds (17), (29) and (30) was 0.1 mg/kg, and for compound (19) 0.01 mg/kg s.c.

DOPAMINE RECEPTOR BLOCKING ACTIVITY IN THE CENTRAL NERVOUS SYSTEM

Compounds were tested for inhibition of apomorphine induced climbing in the mouse. The test is based on that described by Protais, P., Constantin, J. and Schwartz, J. C. (1976), Psychopharmacology, 50, 1–6.

Apomorphine 1 mg/kg s.c. induces mice to climb the wall of a wire cage (inverted food hopper—11×7.5×18 cm high). Mice acclimatised in their home cages in groups of 5 are placed under the hoppers immediately after the injection of apomorphine 1 mg/kg s.c. At 10, 20 and 30 minutes after injection climbing behaviour is scored. The mice are observed for 30 seconds and scored according to the position they spend the majority of time in, score 0—four paws on floor of cage; score 1—fore paws only on walls; score 2—all paws on wall of cage. The scores at all 3 times and for each mouse are summed and mice drug treated compared to mice receiving apomorphine only. A saline only treated group is also included and any score, generally >5% of maximum taken into account.

The results were as follows:

| Compound No. | $ED_{50}$ mg/kg s.c. |
| --- | --- |
| 17 | 7.7 |
| 18 | 10 (inactive) |
| 19 | 0.36 |
| 20 | 3.6 |
| 26 | 10 (inactive). |

TOXICITY

No toxic effects were observed in the above tests.

We claim:

1. A compound of formula (I), or a pharmaceutically acceptable salt, quaternary derivative or N-oxide thereof, or a pharmaceutically acceptable solvate of any of the foregoing:

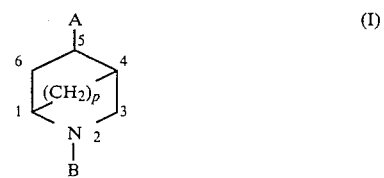

wherein p is 1 to 3;

B is $C_{1-7}$ alkyl, $C_{3-8}$ cycloalkyl, $C_{3-8}$ cycloalkyl-$C_{1-2}$ alkyl, or a group $(CH_2)_t R_{11}$ where t is 1 or 2 and $R_{11}$ is thienyl or furyl optionally substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolysable acyloxy; and (i) A is a group of formula (II):

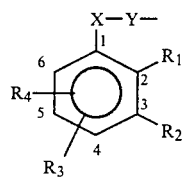 (II)

in which either
(a) one of X and Y is CO and the other is NH; and
R$_1$ is selected from halogen, C$_{1-6}$ alkyl, C$_{1-6}$ alkoxy, C$_{1-6}$ alkylthio, and amino optionally substituted by one or two groups selected from C$_{1-6}$ alkyl, C$_{3-8}$ cycloalkyl, C$_{3-8}$ cycloalkyl C$_{1-4}$ alkyl, phenyl and phenyl C$_{1-4}$ alkyl groups or optionally N,N-disubstituted by C$_{4-5}$ polymethylene; or X is CO and Y is NR$_6$ where R$_1$ and R$_6$ together are C$_{1-2}$ alkylene; and
either R$_2$, R$_3$ and R$_4$ are each independently selected from the class of hydrogen, halogen, CF$_3$, C$_{1-6}$ alkyl, C$_{1-6}$ alkoxy, C$_{1-6}$ alkylthio, C$_{1-7}$ acyl, C$_{1-7}$ carboxylic acylamino, C$_{1-6}$ alkylsulphonylamino, N-(C$_{1-6}$alkyl-sulphonyl)-N-C$_{1-4}$ alkylamino, C$_{1-6}$ alkylsulphonyl, C$_{1-6}$ alkylsulphinyl, hydroxy, nitro, or amino, aminocarbonyl, aminosulphonyl, aminosulphonylamino or N-(aminosulphonyl)-N-C$_{1-4}$ alkylamino optionally N-substituted by one or two groups selected from C$_{1-6}$ alkyl, C$_{3-8}$ cycloalkyl, C$_{3-8}$ cycloalkyl C$_{1-4}$ alkyl, phenyl and phenyl C$_{1-4}$ alkyl or optionally N,N-disubstituted by C$_{4-5}$ polymethylene; or one of R$_2$, R$_3$ and R$_4$ is selected from the foregoing class and the remaining two of R$_2$, R$_3$ and R$_4$ when on adjacent atoms are together C$_{1-2}$ alkylenedioxy; or
(b) one of X and Y is CO and the other is NH; R$_1$ and R$_2$ together are C$_{1-2}$ alkylenedioxy or C$_{1-2}$ oxyalkylenethio, or C$_{2-3}$ alkyleneoxy in which the oxygen atom is attached to the ring at the 2-position; as depicted in formula (II); and
R$_3$ and R$_4$ are each independently selected from the class of values recited hereinbefore for R$_2$, R$_3$ and R$_4$ in paragraph (i) (a) hereinbefore or when on adjacent atoms are together C$_{1-2}$ alkylenedioxy; or
(ii) A is a group of formula (III):

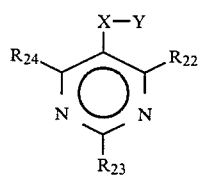 (III)

in which
one of X and Y is CO and the other is NH; and
R$_{22}$, R$_{23}$ and R$_{24}$ are each independently selected from the class of values of the variables R$_2$, R$_3$ and R$_4$ as defined hereinbefore in paragraph (i) (a) in relation to formula (II), except C$_{1-2}$ alkylenedioxy.

2. A compound according to claim 1 of formula (IV):

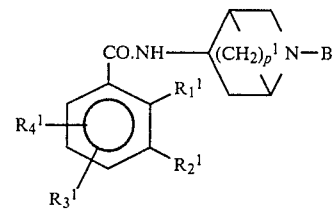 (IV)

wherein
either R$^1$$_1$ is C$_{1-6}$ alkoxy or amino optionally N-substituted by one or two groups selected from C$_{1-6}$ alkyl or C$_{3-8}$ cycloalkyl or optionally N,N-disubstituted by C$_{4-5}$ polymethylene; and
one of R$^1$$_2$, R$^1$$_3$ and R$^1$$_4$ is hydrogen and the other two are independently selected from the class of hydrogen, amino optionally substituted by one or two C$_{1-6}$ alkyl groups or N,N-disubstituted by C$_{4-5}$ polymethylene, carboxylic C$_{1-7}$ acylamino, chloro, bromo, trifluoromethyl, hydroxy, C$_{1-6}$ alkoxy, C$_{1-6}$ alkylthio, C$_{1-6}$ alkyl, C$_{1-6}$ alkylsulphonyl, C$_{1-6}$ alkylsulphinyl or aminosulphonyl optionally N-substituted by one or two C$_{1-6}$ alkyl group or N,N-disubstituted by C$_{4-5}$ polymethylene; or
R$^1$$_1$ and R$^1$$_2$ together are methylenedioxy or ethylenedioxy and R$^1$$_3$ and R$^1$$_4$ are the same or different and are selected from the class of substituent hereinbefore defined for R$^1$$_2$, R$^1$$_3$ and R$^1$$_4$;
p$^1$ is 1 or 2; and
B is as defined in claim 1.

3. A compound according to claim 1 of formula (V):

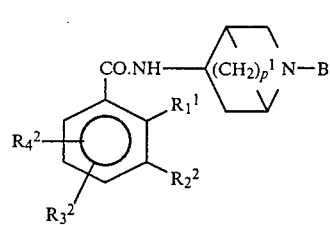 (V)

wherein
R$^1$$_1$, p$^1$ and B are as defined in claim 2 and one of R$^2$$_2$, R$^2$$_3$ and R$^2$$_4$ is hydrogen, and the other two are independently selected from hydrogen, amino, carboxylic C$_{1-7}$ acylamino, chloro, bromo, trifluoromethyl, hydroxy, C$_{1-6}$ alkoxy, C$_{1-6}$ alkylthio and C$_{1-6}$ alkyl.

4. A compound according to claim 1 of formula (VI):

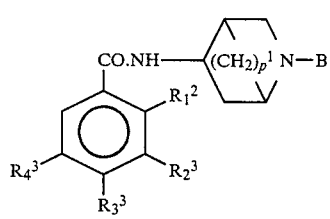 (VI)

wherein
p$^1$ and B are as defined in claim 2
R$^3$$_3$ is hydrogen or amino;

$R^3_4$ is $C_{1-6}$ alkylsulphonyl, $C_{1-6}$ alkylsulphinyl, or aminosulphonyl optionally N-substituted by one or two $C_{1-6}$ alkyl groups or $C_{4-5}$ polymethylene; and either $R^2_1$ is $R^1_1$ as hereinbefore defined and $R^2_2$ is hydrogen; or $R^2_1$ and $R^3_2$ together are $C_{2-3}$ alkylenedioxy.

5. A compound according to claim 1 which is selected from the compounds: axial isomer of (±)-4-amino-5-chloro-2-methoxy-N-(5-[2-methyl-2-azabicyclo[2,2,2]octyl]benzamide, the equatorial isomer of (±)-4-amino-5-chloro-2-methoxy-N-(5-[2-methyl-2-azabicyclo[2,2,2]octyl]benzamide, the axial isomer of (±)-4-amino-5-chloro-2-methoxy-N-(5-[2-benzyl-2-azabicyclo[2,2,2]octyl]benzamide, the equatorial isomer of (±)-4-amino-5-chloro-2-methoxy-N-(5-[2-benzyl-2-azabicyclo[2,2,2]octyl]-benzamide, the equatorial isomer of (±)-4-amino-5-chloro-2-methoxy-N-[5-(2-methyl-2-azabicyclo[2.2.1]heptyl)-]benzamide, the axial isomer of (±)-4-amino-2-methoxy-5-methylsulphonyl-N-[5-(2-benzyl-2-azabicyclo[2.2.2]octyl)-]benzamide, the equatorial isomer of (±)-4-amino-2-methoxy-5-methylsulphonyl-N-[5-(2-benzyl-2-azabicyclo[2.2.-2]octyl)]benzamide, or a pharmaceutically acceptable salt, quaternary derivative or N-oxide thereof or a pharmaceutically acceptable solvate of any of the foregoing.

6. A compound according to claim 1 which is the equatorial isomer of (±)4-amino-5-chloro-2-methoxy-N-[5-(2-methyl-2-azabicyclo[2.2.1]heptyl]benzamide hydrochloride or
the equatorial isomer of (±)4-amino-2-methoxy-5-methylsulphonyl-N-[5-(2-benzyl-2-azabicyclo[2.2.-2]octyl]benzamide hemihydrate.

7. A compound according to claim 1 which is the axial isomer of (±)-4-amino-5-chloro-2-methoxy-N-(5-[2-methyl-2-azabicyclo[2,2,2]octyl]benzamide, or the equatorial isomer of (±)-4-amino-5-chloro-2-methoxy-N-(5-[2-methyl-2-azabicyclo[2,2,2]octyl]benzamide, or the hydrochloride salt thereof.

8. A pharmaceutical composition comprising a compound of formula (I) according to claim 1, or a pharmaceutically acceptable salt, quaternary derivative or N-oxide thereof, or a pharmaceutically acceptable solvate of any of the foregoing, and a pharmaceutically acceptable carrier.

9. A compound of formula (VIII):

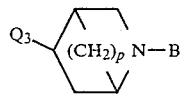

(VIII)

wherein

B and p are as defined in claim 1; and $Q_3$ is $NH_2$ or $COQ_4$ where $Q_4$ is a group displaceable by a nucleophile; or a compound of formula (X):

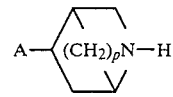

(X)

wherein the variables are as defined in claim 1.

10. A method of treatment or prophylaxis of emesis or disorders of the central nervous system in mammals, such as humans, which comprises the administration of an effective amount of a compound according to claim 1 of formula (I), or a pharmaceutically acceptable acid addition salt thereof, or a pharmaceutically acceptable solvate of either of the foregoing.

11. A method of treatment or prophylaxis of disorders related to impaired gastro-intestinal motility in mammals, such as humans, which comprises the administration of an effective amount of a compound according to claim 1 of formula (I) or a pharmaceutically acceptable salt, quaternary derivative or N-oxide thereof, or a pharmaceutically acceptable solvate of any of the foregoing.

* * * * *